(12) United States Patent
Radrich et al.

(10) Patent No.: US 11,621,082 B2
(45) Date of Patent: Apr. 4, 2023

(54) PHYSIOLOGICAL PARAMETER MONITORING SYSTEM

(71) Applicant: DRÄGERWERK AG & CO. KGA, Lübeck (DE)

(72) Inventors: Karin Radrich, Melrose, MA (US); Frank Franz, Stockelsdorf (DE); Carolyn Lall, Terra Cotta (CA)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 500 days.

(21) Appl. No.: 16/474,770

(22) PCT Filed: Dec. 28, 2016

(86) PCT No.: PCT/US2016/068846
§ 371 (c)(1),
(2) Date: Jun. 28, 2019

(87) PCT Pub. No.: WO2018/125077
PCT Pub. Date: Jul. 5, 2018

(65) Prior Publication Data
US 2021/0287803 A1 Sep. 16, 2021

(51) Int. Cl.
*G16H 50/30* (2018.01)
*A61B 5/00* (2006.01)
*A61B 5/0205* (2006.01)

(52) U.S. Cl.
CPC ........... *G16H 50/30* (2018.01); *A61B 5/0004* (2013.01); *A61B 5/0024* (2013.01); *A61B 5/0205* (2013.01); *A61B 5/7275* (2013.01); *A61B 5/742* (2013.01); *A61B 5/7405* (2013.01); *A61B 5/746* (2013.01); *A61B 5/7435* (2013.01); *A61B 5/7455* (2013.01)

(58) Field of Classification Search
CPC ...... G16H 50/20; G16H 50/30; A61B 5/0024; A61B 5/7275; A61B 5/742; A61B 5/0205
USPC .................................................. 600/300, 301
See application file for complete search history.

(56) References Cited

U.S. PATENT DOCUMENTS

| | | |
|---|---|---|
| 2007/0118054 A1 | 5/2007 | Pinhas et al. |
| 2012/0286955 A1 | 11/2012 | Welch et al. |
| 2013/0116578 A1 | 5/2013 | An et al. |
| 2013/0211214 A1 | 8/2013 | Olsen |
| 2016/0220127 A1* | 8/2016 | Boyer .................... G16H 50/30 |

OTHER PUBLICATIONS

International Search Report dated Sep. 19, 2017 in International Application No. PCT/US2016/068846.

* cited by examiner

*Primary Examiner* — John R Downey
(74) *Attorney, Agent, or Firm* — Nolte Lackenbach Siegel

(57) ABSTRACT

Data streams are received from each of the plurality of sensors. These data streams comprise varying values generated by in the sensors and characterize an associated physiological parameter. A parameter score is repeatedly determined for each physiological sensor that is based on whether the varying values for the associated physiological parameter deviate from at least one pre-defined threshold. A patient health index is repeatedly generated by combining each of the determined parameter scores to characterize an overall health of the patient. Data characterizing the patient health index is repeatedly provided. Related apparatus, systems, techniques and articles are also described.

15 Claims, 15 Drawing Sheets

PHYSIOLOGICAL PARAMETER MONITORING SYSTEM

CROSS-REFERENCE TO RELATED APPLICATIONS

This Application is a 371 Application of International Patent Application Serial No. PCT/US2016/068846, entitled, "PHYSIOLOGICAL PARAMETER MONITORING SYSTEM, filed Dec. 28, 2016.

TECHNICAL FIELD

The subject matter described herein relates to physiological parameter monitoring systems and related methods, including graphical user interfaces, for characterizing health of a patient as measured by a plurality of physiological sensors coupled to a patient monitor.

BACKGROUND

The assessment of a patient's current health status by a health care professional is typically performed by observation of the patient's vital signs, such as blood pressure, heart rate, respiratory rate, blood oxygenation and the like as measured by various physiological sensors and as displayed by a patient monitor. These physiological parameters are measured and displayed separately, but compared against each other and evaluated in their entirety by the health care professional based on his or her clinical experience.

SUMMARY

In one aspect, a system includes a communications interface, at least one programmable data processor, and memory. The communications interface is configured to receive data streams from a plurality of physiological sensors with each sensor measuring a different physiological parameter of a patient. The memory can store instructions which, when executed by the at least one programmable data processor, result in various operations. These operations can include receiving one or more data streams from each of the plurality of sensors via the communications interface. The one or more data streams can include varying values generated by the sensor and characterizing the associated physiological parameter. The operations can also include repeatedly determining, for each physiological sensor, a parameter score based on whether the varying values for the associated physiological parameter deviate from at least one pre-defined threshold. The operations can also include repeatedly generating a patient health index by combining each of the determined parameter scores to characterize an overall health of the patient. Further, the operations can include repeatedly providing data characterizing the patient health index.

The repeatedly determining, repeatedly generating and repeatedly providing can be performed on a periodic basis.

The repeatedly determining, repeatedly generating and repeatedly providing can, in some variations, be performed on a continuous basis.

The providing data can include one or more of: displaying the data characterizing the patient health index in an electronic display device, loading the data characterizing the patient health index into the memory, storing the data characterizing the patient health index in persistent memory, transmitting the data characterizing the patient health index to a remote computing system, or generating an audio, vibrational and/or visual alert characterizing the patient health index.

A magnitude of the deviations from the at least one pre-defined threshold can be repeatedly calculated, and factors can be repeatedly allocated to the magnitude of the deviations which are used to generate the determined parameter scores. The allocated factors can be time-averaged over a pre-defined time window and they can be used to generate the determined parameter scores.

The generation of the patient health index can assign weights to each of the determined parameter scores as part of the combining. The weights can vary depending on an amount of time and/or a severity of deviation from the at least one pre-defined threshold.

Segments of time can be identified during which the values in the data streams are unreliable. In response, the associated parameter score for the corresponding physiological sensor can be adjusted to exclude such identified segments. The adjusting can include using values from preceding or successive segments of time relative to the identified segments of time for the identified segment of time when generating the associated parameter score. In addition or the alternative, the adjusting can include using factors from preceding or successive segments of time relative to the identified segments of time for the identified segment of time when generating the associated parameter score.

In some implementations, the providing of data can include displaying, in a graphical user interface, a visualization displaying the repeatedly generated patient health index over time in relation to the repeatedly determined parameter scores. Such a visualization can further displays parameter scores used to generate the repeatedly determined patient health index. A color of at least a portion of the visualization can vary depending on the allocated factors. The visualization can further display at least one of the pre-defined thresholds. Further, a color of at least a portion of the visualization can varies depending on deviations from the pre-defined thresholds.

In an interrelated aspect, data streams are received from each of the plurality of sensors. These data streams comprise varying values generated by the sensors and characterize an associated physiological parameter. A parameter score is repeatedly determined for each physiological sensor that is based on whether the varying values for the associated physiological parameter deviate from at least one pre-defined threshold. A patient health index is repeatedly generated by combining each of the determined parameter scores to characterize an overall health of the patient. Data characterizing the patient health index is repeatedly provided.

Non-transitory computer program products (i.e., physically embodied computer program products) are also described that store instructions, which when executed by one or more data processors of one or more computing systems, cause at least one data processor to perform operations herein. Similarly, computer systems are also described that can include one or more data processors and memory coupled to the one or more data processors. The memory can temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g., the Internet, a wireless wide area network, a local area network, a wide area network, a wired network, or the like), via a direct connection between one or more of the multiple computing systems, etc.

The subject matter described herein provides many technical advantages. For example, the current subject matter provides techniques for characterizing and visualizing a current wellbeing of a patient that takes into account dynamically changing individual patient characteristics, development over time, and knowledge of the history and diagnosis of the patient.

The details of one or more variations of the subject matter described herein are set forth in the accompanying drawings and the description below. Other features and advantages of the subject matter described herein will be apparent from the description and drawings, and from the claims.

DETAILED DESCRIPTION

The current subject matter is directed to a physiological monitoring system that characterizes the health of a patient based on multiple, dynamically changing physiological parameters as measured by various physiological sensors connected to the patient and to a patient monitor.

Figure 1:
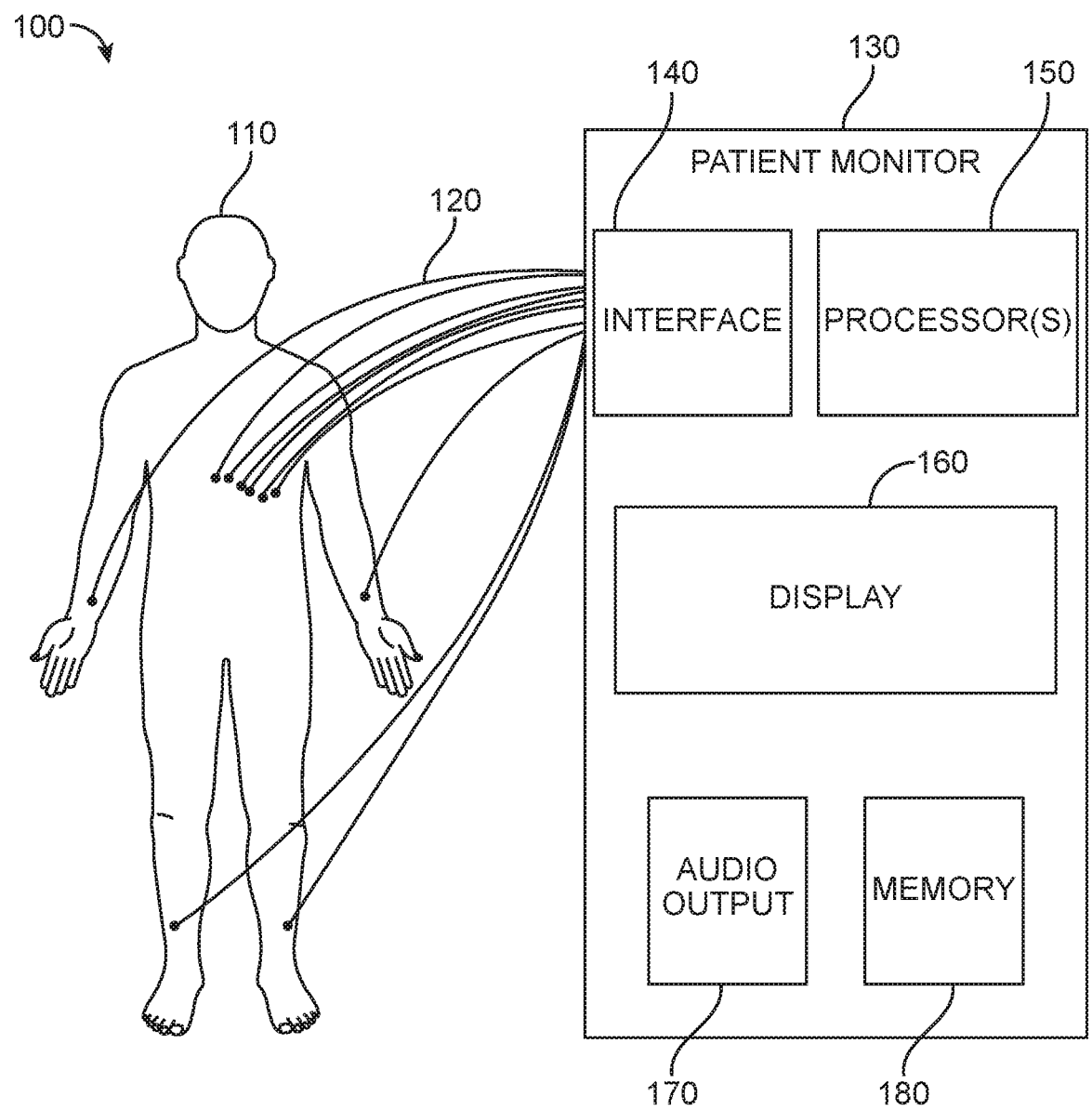
FIG. 1 is a schematic diagram illustrating a patient monitor coupled to a patient.

FIG. 1 is a diagram 100 illustrating an example implementation in which physiological parameters of a patient, including, for example, blood pressure, heart rate, respiratory rate, and blood oxygenation of a patient 110 are measured by a patient monitor 130. The patient monitor 130 can include memory 180 for storing instructions for execution by one or more processor/processor cores 150. Memory 180 can also be capable of storing parameter data and related visualizations. The patient monitor 130 can include a display 160 for rendering visual information that corresponds to the physiological parameters (e.g., values, waveforms, etc.). In addition, the patient monitor 130 can also include an interface 140 that permits for wired or wireless communication with one or more physiological sensors 120 and/or a remote medical device and/or a remote computing system or network to transmit/receive physiological parameter data (e.g., vital signs, etc.). One example, of a physiological sensor 120 is an electrocardiogram (ECG) electrode set that includes, for example, a right arm electrode, a left arm electrode, and a left leg electrode. Other types of physiological sensors 120 include, for example, invasive blood pressure transducers, blood oxygenation (e.g., SpO2 finger cuff, etc.), and respiration sensors (i.e., to detect, for example, apnea and other breathing abnormalities, etc.). The physiological sensors 120 can each transmit/generate one or more data streams to the communications interface 140. These data streams can include varying values generated by the physiological sensor 120 that characterize the associated physiological parameter (e.g., varying vital signs for the patient, etc.).

Patient monitor 130 can transmit data characterizing the physiological parameters of the patient 110 to a remote computing system (e.g., medical device, back-end computing system, etc.) via the communications interface 140. Patient monitor 130 can also include an audible alarm that can sound from an audio output 170 alerting a patient and/or medical staff Alarms can also be conveyed by via the display 160 or other visual alert mechanisms (not shown).

The patient monitor 130 can, using the data streams received by the interface from the physiological sensors 120 and the processor(s) 150, implement, an algorithm for calculating a patient health index (PHI). The algorithm can weigh deviations of the varying values for the associated physiological parameter from at least one pre-defined threshold (sometimes referred to herein as limit violations) depending on the severity/magnitude of the respective deviation (e.g., warning, serious, safety, etc.). The average of the weights over a predefined time period can result in a parameter score, and a combination of these scores for different physiological parameters can results in the patient health index (which dynamically changes). The patient health index is a measure for the current health status of the patient which also gives an indication about status development of the patient towards health improvement or deterioration. This information allows for better judgment of the current status and the future heath development of the patient.

Figure 2:
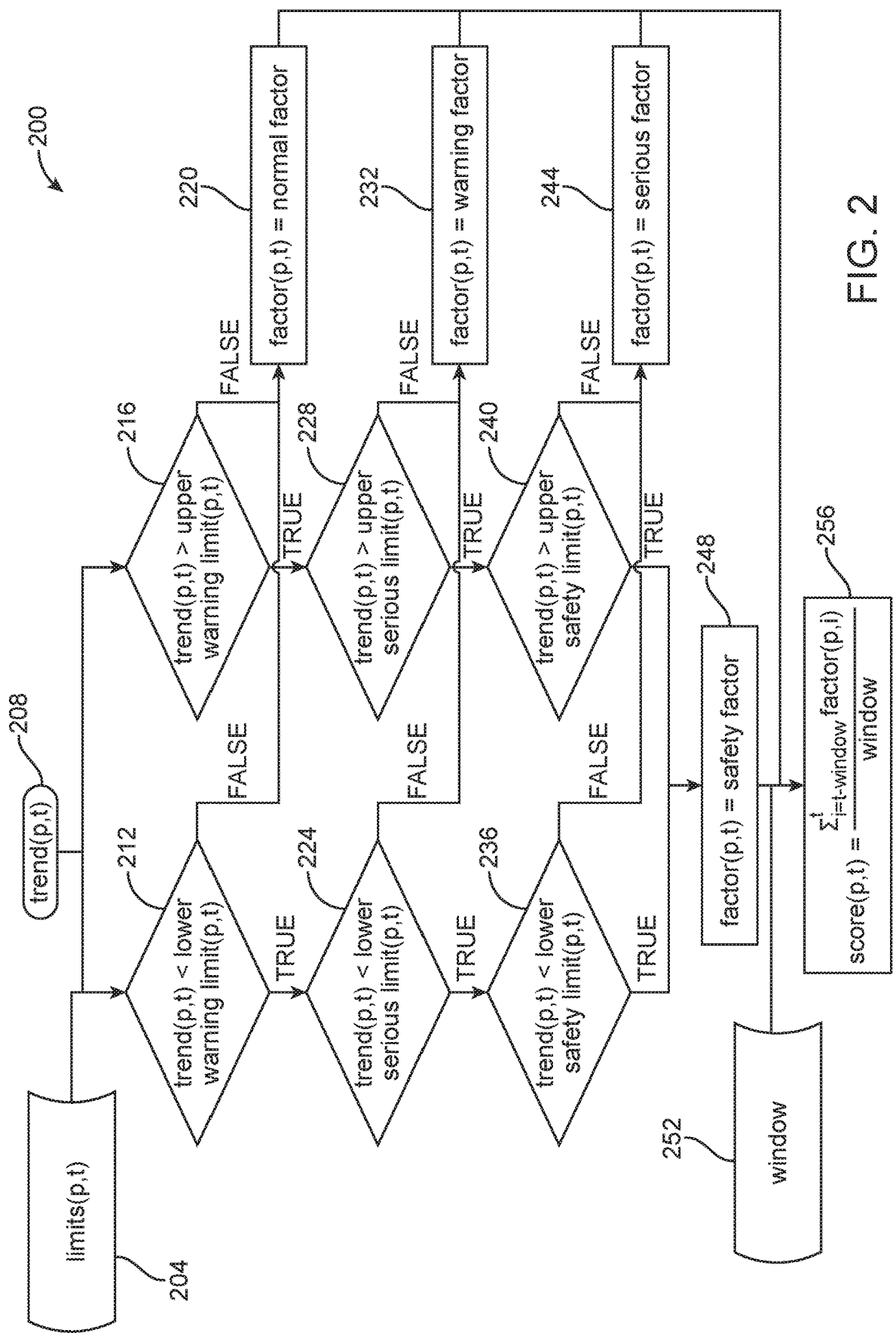
FIG. 2 is a process flow diagram illustrating calculation of a physiological parameter score.

FIG. 2 is a process flow diagram 200 illustrating implementation of an algorithm for calculating a patient health index. Initially a score for each individual parameter is computed based on the individual upper and lower alarm limit values considered appropriate for the respective patient based on his/her diagnosis and assessment when admitted to the hospital. More than one upper and lower alarm limit can be defined representing increasing parameter deviation from normal physiological levels and therefore increasing health risk. The algorithm weights every limit violation depending on the severity of the respective violation (in this example three limits are used, denominated as warning, serious, and safety limits; warning representing a low, serious a medium, and safety a high patient health risk limit). For example, an initial status value of 100% (trend within normal physiological range) is reduced by a factor f1, f2 or f3 based on the magnitude of the deviation from the normal range. For example, if the trend comes to lie between warning and serious limits, the initial value is multiplied by factor f1 (say by 0.7, reducing the status value to 70%), if the parameter value further worsens and comes to lie between serious and safety limits it is multiplied by another factor f2 indicative of the worsening (say by 0.3, reducing the status value to 30%), if it crosses the safety threshold the status value drops to 0%.

With continued reference to diagram 200 of FIG. 2, initially limits 204 are defined (for example, using default values and/or by the healthcare professional inputting values into a graphical user interface, or by (semi-)automatic determination through an algorithm). Trend information 208 which is or is derived from the data streams outputted by the physiological sensors 120 is analyzed to determine whether the values within such data streams exceed respective thresholds 212, 216; 224, 228; and 236, 240 which respectively correspond to categories of factors 232, 244, 248 (which in this example correspond to warning factor, serious factor, and safety factor). If none of the thresholds are exceeded, then a normal factor 220 can be assigned at any given moment. Further, a window 252 can be defined/established which specifies a time interval before t for computation of the physiological parameter score. The physiological parameter score 256 can then be calculated as an average of the factors over the window. The physiological parameter score 256 can be continuously calculated or alternatively on a periodic or on-demand basis.

Figure 3:
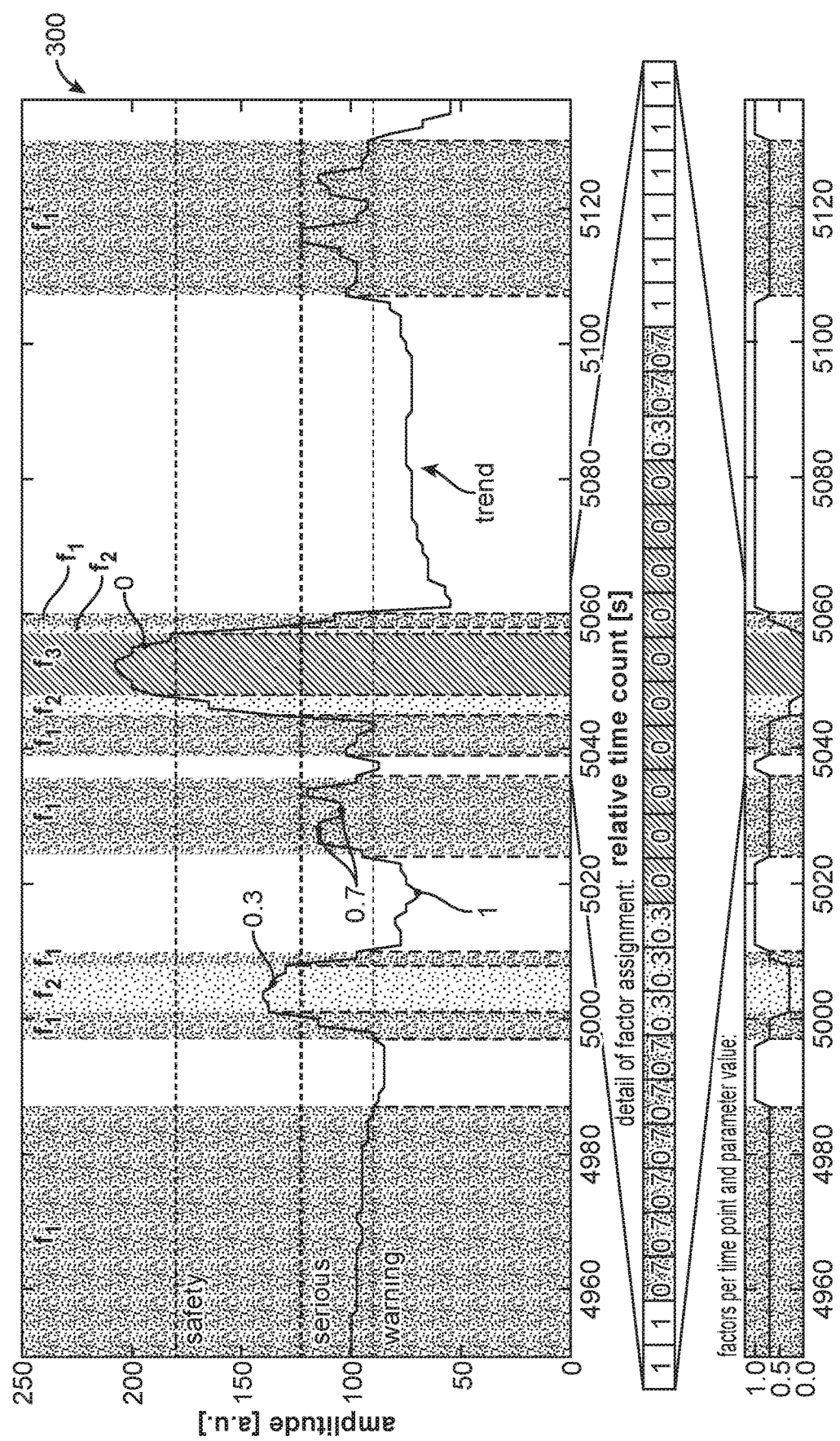
FIG. 3 is a diagram illustrating a methodology of allocation of factors to values from data streams generated by one or more physiological sensors.

The result of the factor allocation of FIG. 2 is shown in diagram 300 of FIG. 3 for an arbitrary physiological parameter trend. Diagram 300 can, for example, be a view rendered in a graphical user interface displayed on the display 160 of patient monitor 130. The allocated factors per time point are shown in the graph at the bottom. The trend starts with a warning limit violation and is therefore allocated factor f1 (in this example 0.7). When the trend goes back below the warning limit the status value in the lower graph increases to 1 (i.e. 100%, normal factor). Subsequent limit violations of the serious limit and safety limit are consequently allocated the respective factors f2 and f3 for the duration of the violation.

Figure 4:
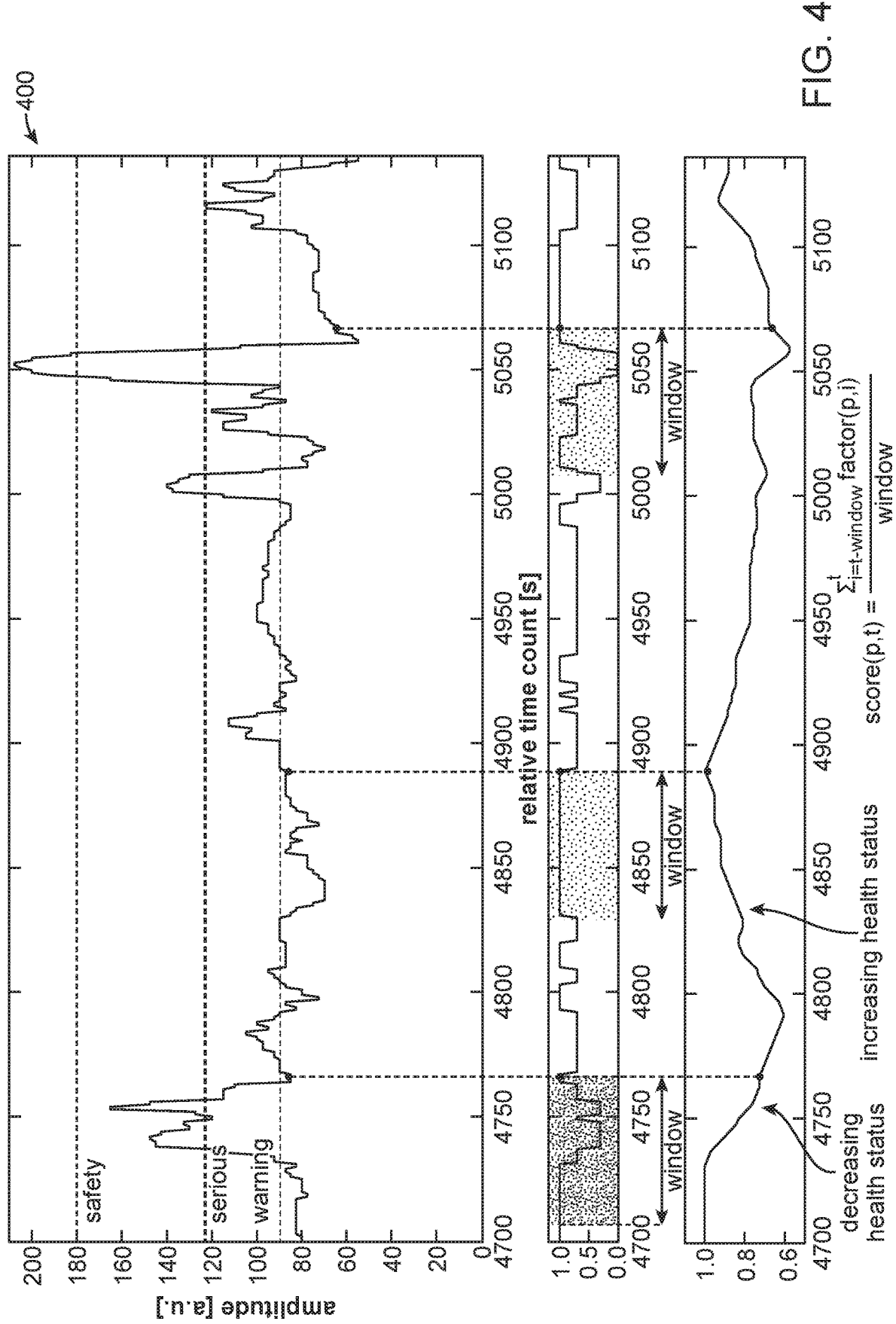
FIG. 4 is a diagram illustrating allocation of a final physiological parameter score based on allocated factors of values from data streams generated by one or more physiological sensors.

The final physiological parameter score for one time point can be obtained by averaging the factors over a time window preceding that time point as illustrated in diagram 400 of FIG. 4 (which can also be rendered in a graphical user interface displayed on display 160 of the patient monitor 130). This diagram 400 illustrates a measure of the relative time that a parameter is within normal physiological ranges during the past time window. Averaging can help dampen strong influence of short term changes or artifacts on the overall status assessment. Time windows can be of different length such as 30, 60, 90 minutes, and the like. The resulting score graph allows an interpretation of the current physiological parameter status in which its slope gives an indication about the development of the parameter compared to previous times points. A negative slope indicates that new time points added to the averaging time window contribute negatively to the patient score, i.e. increasing parts of the observed trend violate some limit compared to previous time points, and the overall score is therefore decreasing. Conversely, a positive slope indicates that new time points contributing to the score add trend values that are within normal physiological limits, or at least deviate less from the warning limit.

Figure 5:
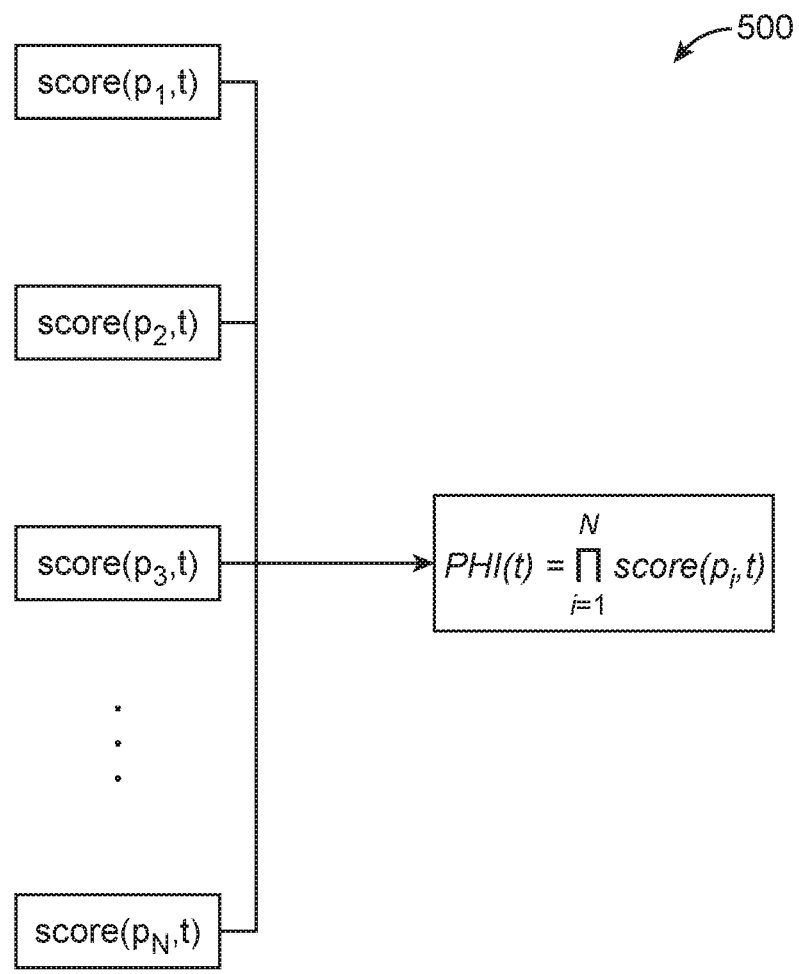
FIG. 5 is a diagram illustrating generation of a patient health index from a plurality of physiological parameter scores.
Figure 6:
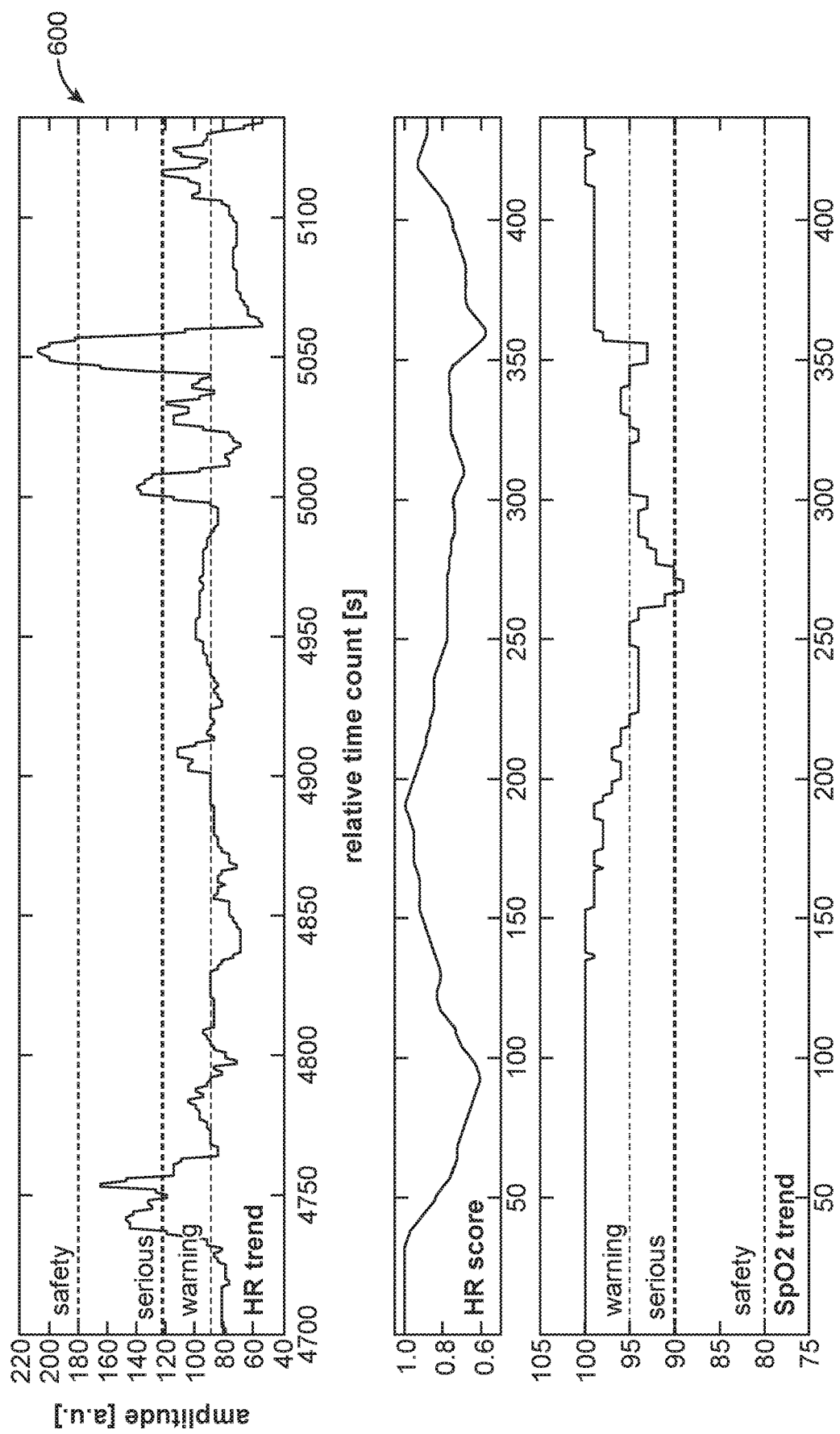
FIG. 6 is a diagram illustrating individual physiological parameters with associated parameter scores and an overall patient health index.
Figure 6:
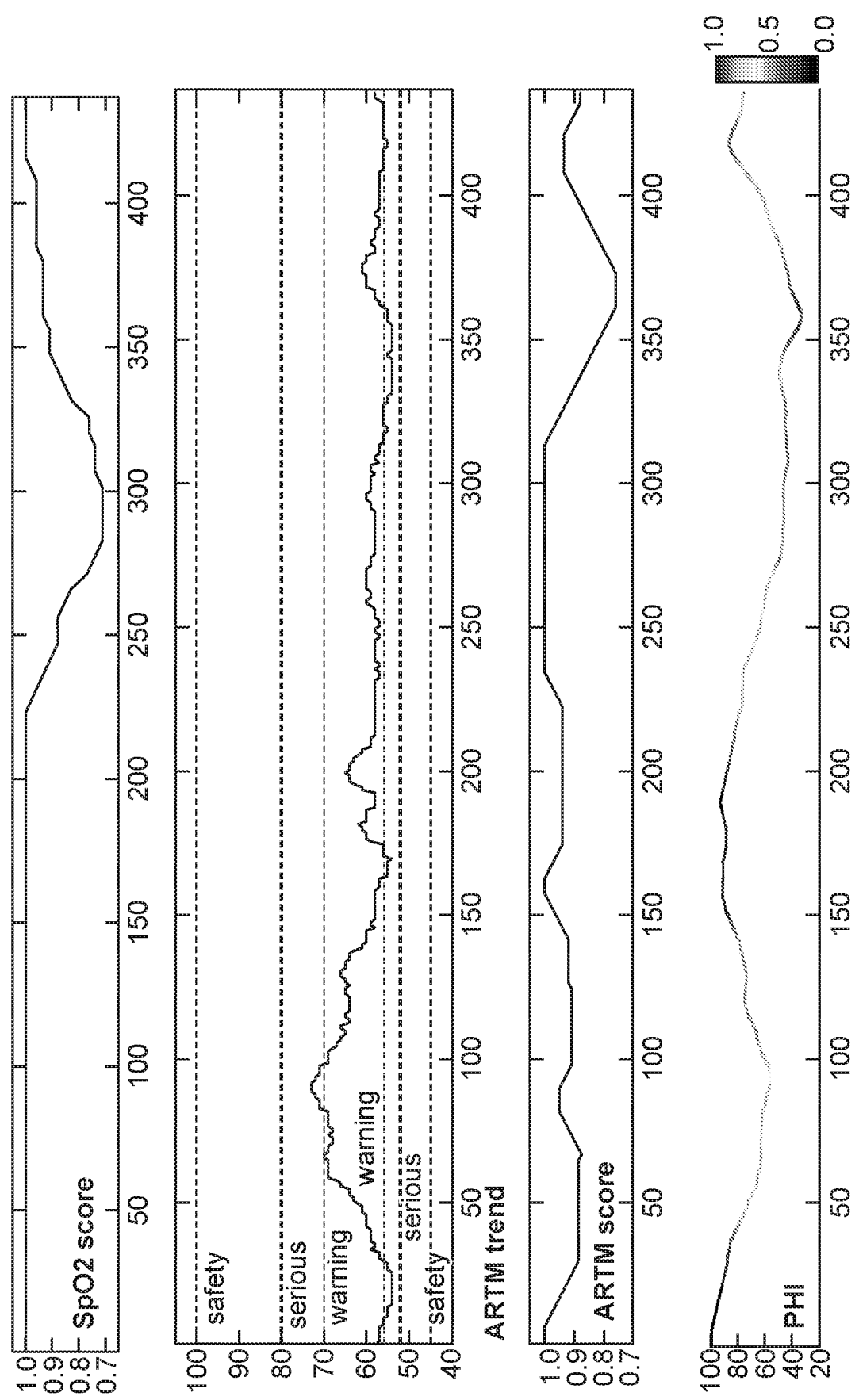

The scores of each parameter (i.e. the averaged factor values) can then be combined for each time point into an overall patient health index (PHI). Such a combination can be done in a variety of manners including multiplication as illustrated in diagram 500 of FIG. 5. Diagram 600 of FIG. 6 illustrates how the individual physiological parameters with associated parameter scores can be combined to form the PHI. For example, if the parameters heart rate, SpO2 and mean arterial pressure are measured, and they have respective individual scores of 70%, 70%, and 100%, then the combined score would be (0.7*0.7*1)*100%=49%. The combination reflects and reproduces the integrated evaluation of multiple parameters by the healthcare professional. Small deviations from normal values for one single parameter may not represent danger for the patient, however small simultaneous deviations of several parameters may indicate some relevant physiological changes for which the healthcare professional should be alerted. By multiplication, small deviations of several parameters amplify each other and result in a larger decrease of the PHI.

Using the algorithm provided herein, all available physiological measurements can be combined by the patient monitor 130 to assess patient status without requirement of specific parameters. The healthcare professional can choose to include all measured parameters or discard those that are irrelevant or might falsify the patient health index, depending on individual diagnosis and medication. The status computation depends on the individually selected/computed alarm limits for each patient and therefore adapts to the specific condition. Averaging allows for evaluation of patient status over a time period and therefore for the estimation of the status development towards improvement or decline of patient health.

In addition to the patient health index computation described above, the patient monitor 130 can implement variations based on the individual preferences in different intensive care units, patient assessment, diagnosis and the like. One such variation can take into account the relevance of different physiological parameters (as measured by the physiological sensors 120) for different diagnoses. Some health conditions may require one physiological parameter to have higher relevance than others. Such a physiological parameter can be assigned a weight in the multiplication process to better reflect its criticality to the patient condition.

In addition to user-specified weights, weights can be assigned by the patient monitor 130 through automated analysis of the parameter trend. A parameter value that is very close to the upper/lower limit for a long time before actually crossing it is more likely to represent a true physiological condition than a parameter value suddenly increasing/decreasing from the center of the value range considered as physiologically normal (sudden change could be due to artifact). The time spent within a margin region below/above the upper/lower limit is hence analyzed and used for assignment of weights. An example of such analysis is shown in diagram 700 of FIG. 7.

Figure 7:
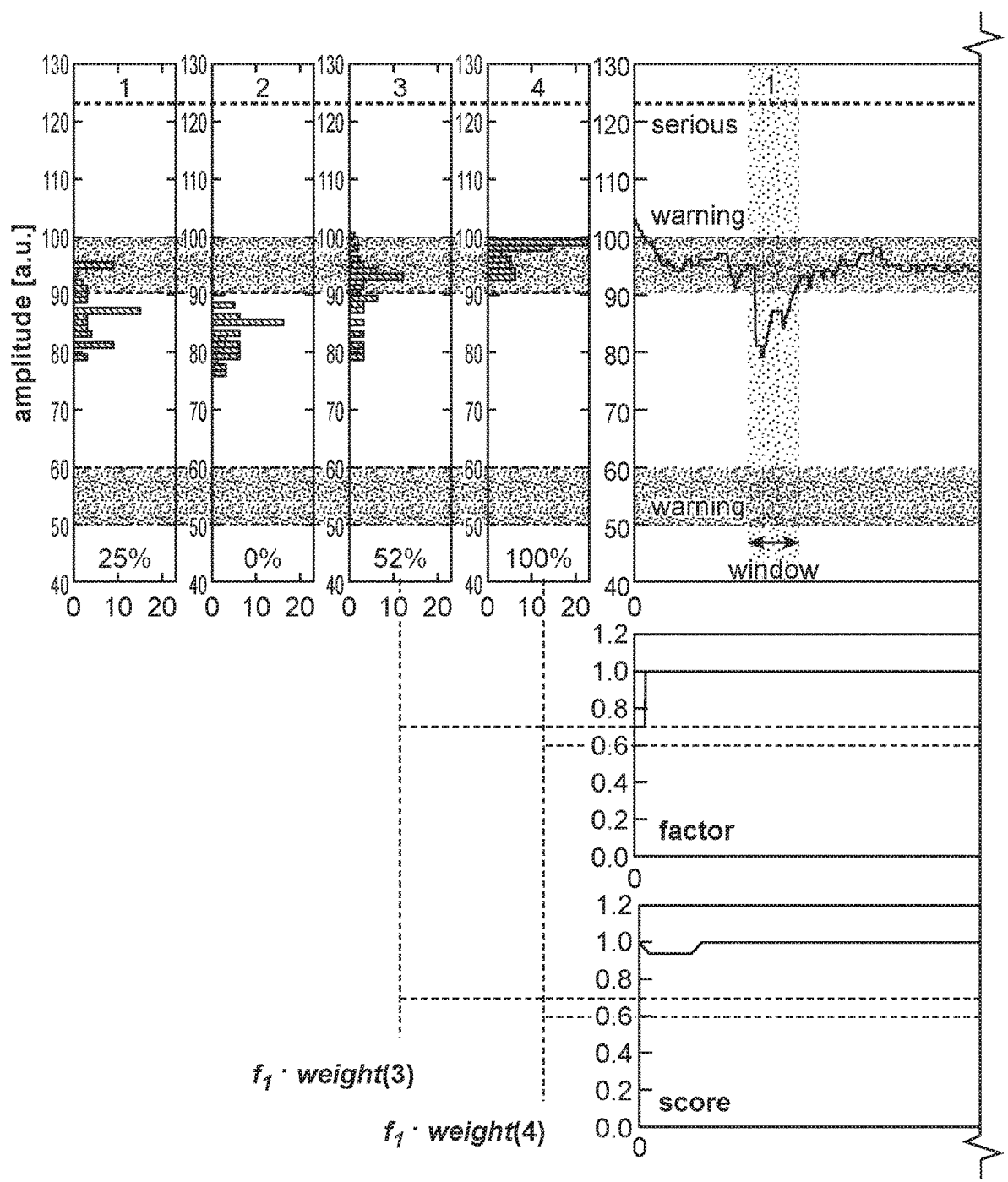
FIG. 7 is a diagram illustrating how weights can be assigned by the patient monitor through automated analysis of physiological parameter trends.
Figure 7:
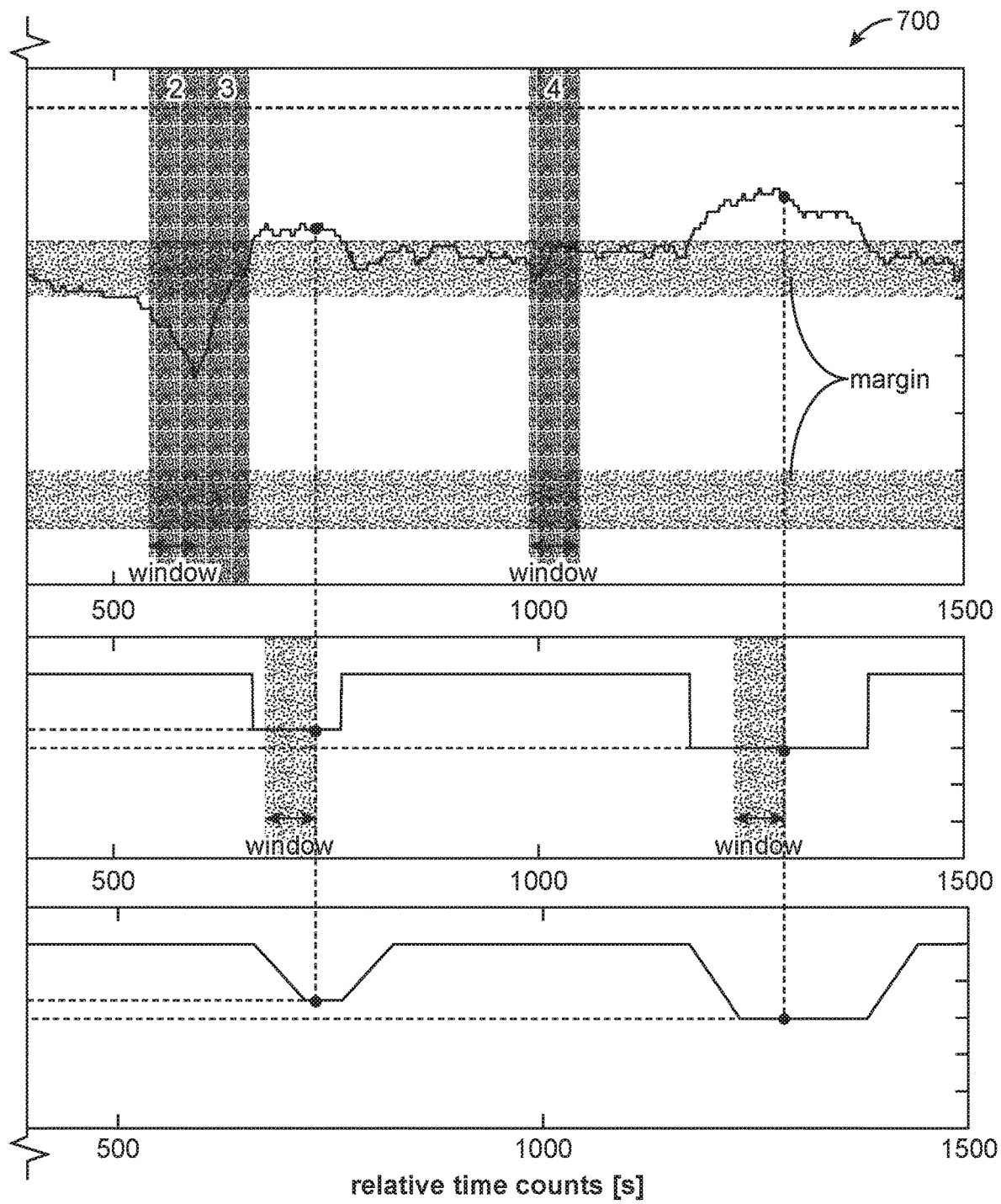

With the example of FIG. 7, the number of samples that are close to the upper/lower limit within the considered time window are counted and compared to the total sample number in the window, resulting in a percentage value that is used for weight allocation. The upper right window shows the trend in which four time windows are highlighted and numbered. Histograms counting the number of samples per amplitude within the windows are shown on the left labeled with the respective number of the corresponding time window. Depending on the percentage of the sample points that lie within the margin region) before a limit violation occurs, the weight can be adjusted and multiplied to the factor for the current limit violation. Within time window 1, for instance, only 25% of the trend lies in the margin region. If the trend would cross the warning limit right after the end of time window 1, a weight of 1 would be multiplied to the factor to reflect the mainly non-critical previous parameter trend. The same is valid for time window 3. Approximately half of the parameter values within this window are outside the margin region, so the limit violation right afterwards is only assigned its regular factor. However, looking at time window 4, all of the parameter values lie within the margin and this does not change until the next limit violation occurs. The next limit violation therefore is weighted by multiplying a weight <1 to the factor and hence reducing the final parameter score. Long term limit violations can in a similar way lead to an adjustment of the weighting of the respective parameter factors.

In addition to limit violations, the algorithm can take into account other clinically relevant conditions, like arrhythmias and other abnormal heart beats, when computing the patient health index. The factor assignment for the time points affected by such conditions can reflect the urgency and relevance of the condition, in which, for example, events like ventricular fibrillation (high priory, very serious) is directly assigned a factor of zero while less critical events like bigeminy can be factored in with a different value reflecting lower immediate risk. The respective parameter factor value gets overwritten, in this example the heart rate. The computation of the average parameter score and the overall status (PHI) remain the same.

Cardiac conditions that are assessed over longer time periods, like PVC (minutes), HRV (hours) or atrial fibrillation (hours) burden can, in some implementations, not be averaged (because they are inherently long term averages) and can directly be allocated a factor based on the respective burden limits.

If signal quality indices (SQIs) are available, they should be integrated into the computation of the PHI. SQIs can be obtained via various mechanisms, including, for example, setting and testing of logical constraints on the physiological values measured by the physiological sensors 120, feature extraction and analysis, or frequency domain analysis. SQIs can be calculated on a single parameter basis to assess the quality of the signal and can represent the confidence in the calculated parameter values. SQI are often represented as a percentage where 0% means the signal is very noisy and should not be used and 100% is a very clean signal where we expect all calculated parameter values to be accurate. SQIs can be signal to noise ratio calculations, or in the case of ECG, an assessment of the stability of QRS complexes over time (see, for example, U.S. Pat. No. 9,042,973, the contents of which are hereby fully incorporated by reference). SQIs can also be determined in various manners including by using a neural network or other machine learning algorithm that, in turn, uses various features of the signal to determine its quality.

The artifact burden during the chosen computation time window is assessed. The integration of SQIs can depend on the amount of artifacts detected during the time window, i.e. the percentage of time that the respective parameter is subjected to artifacts rather than clean signal. This results in two possible integration arrangement. First, for a time window of e.g. 60 minutes, artifacts that in total result in a few seconds or minutes of noisy signal will not have a strong influence on the final value of the PHI as calculated by the patient monitor 130. The noisy segments can hence be assumed to have the same characteristics as preceding and/or successive time points and the PHI can be computed by replacing the factors of the noisy segments with factor values before/after the noisy segment. Second, in case the parameter exposes long stretches of low SQI, it can be deemed unreliable to reflect real physiological conditions and should not be used for PHI computation by the patient monitor 130. A respective message has to be displayed to the user detailing the parameters included in and excluded from the computation.

Figure 8:
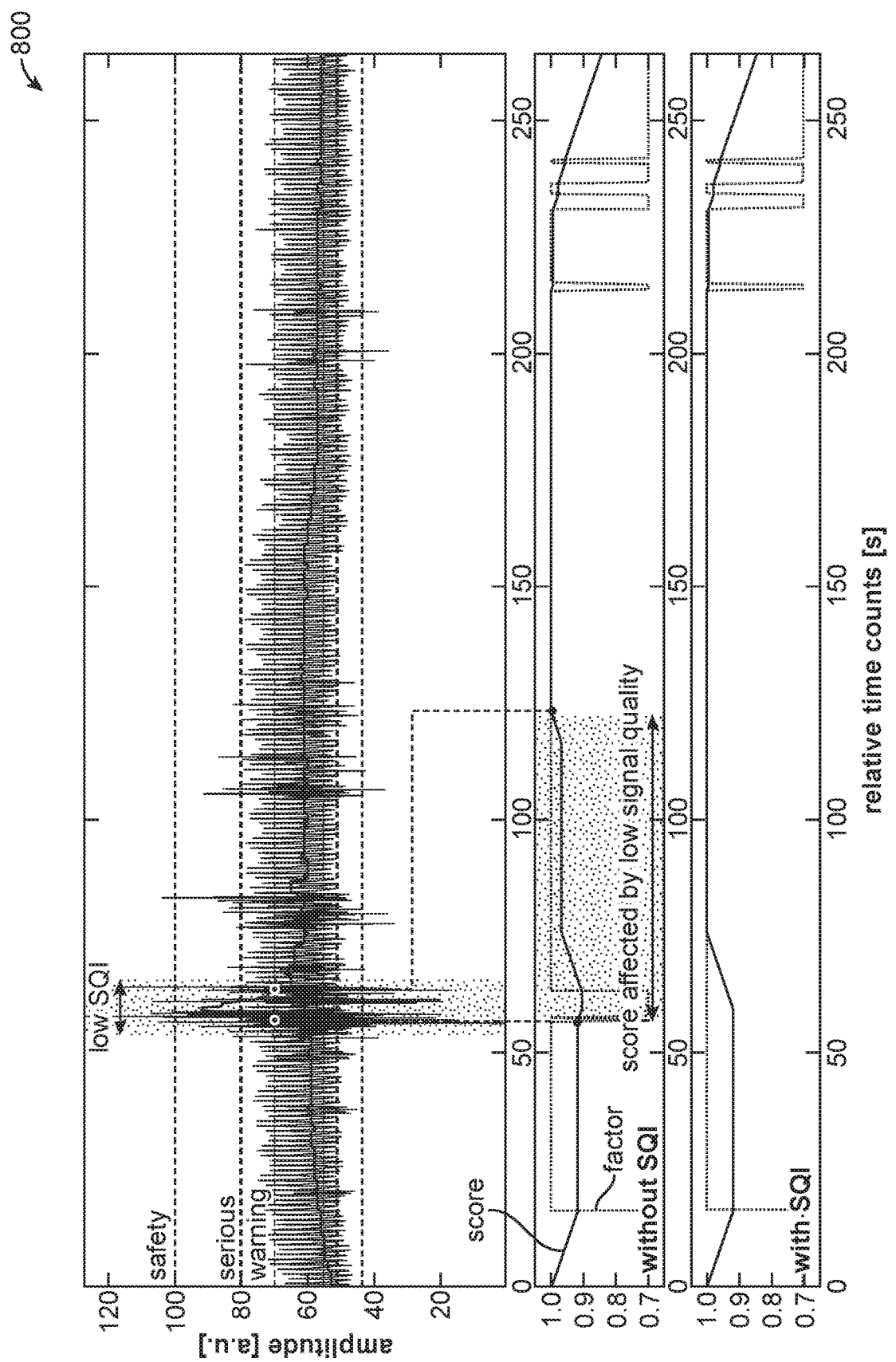
FIG. 8 is a diagram illustrating exclusion of a noisy segment from factor and patient health index computation.

An example for the exclusion of a noisy segment from the factor and score computation is shown in diagram 800 of FIG. 8. The upper window shows an arterial waveform with the dominant noisy segment highlighted, and the mean arterial pressure trend overlaid, as well as all upper and lower limit levels. The score computed ignoring the SQI information is shown in the middle window and the lowest window shows the score if the period of low SQI is excluded.

Figure 9:
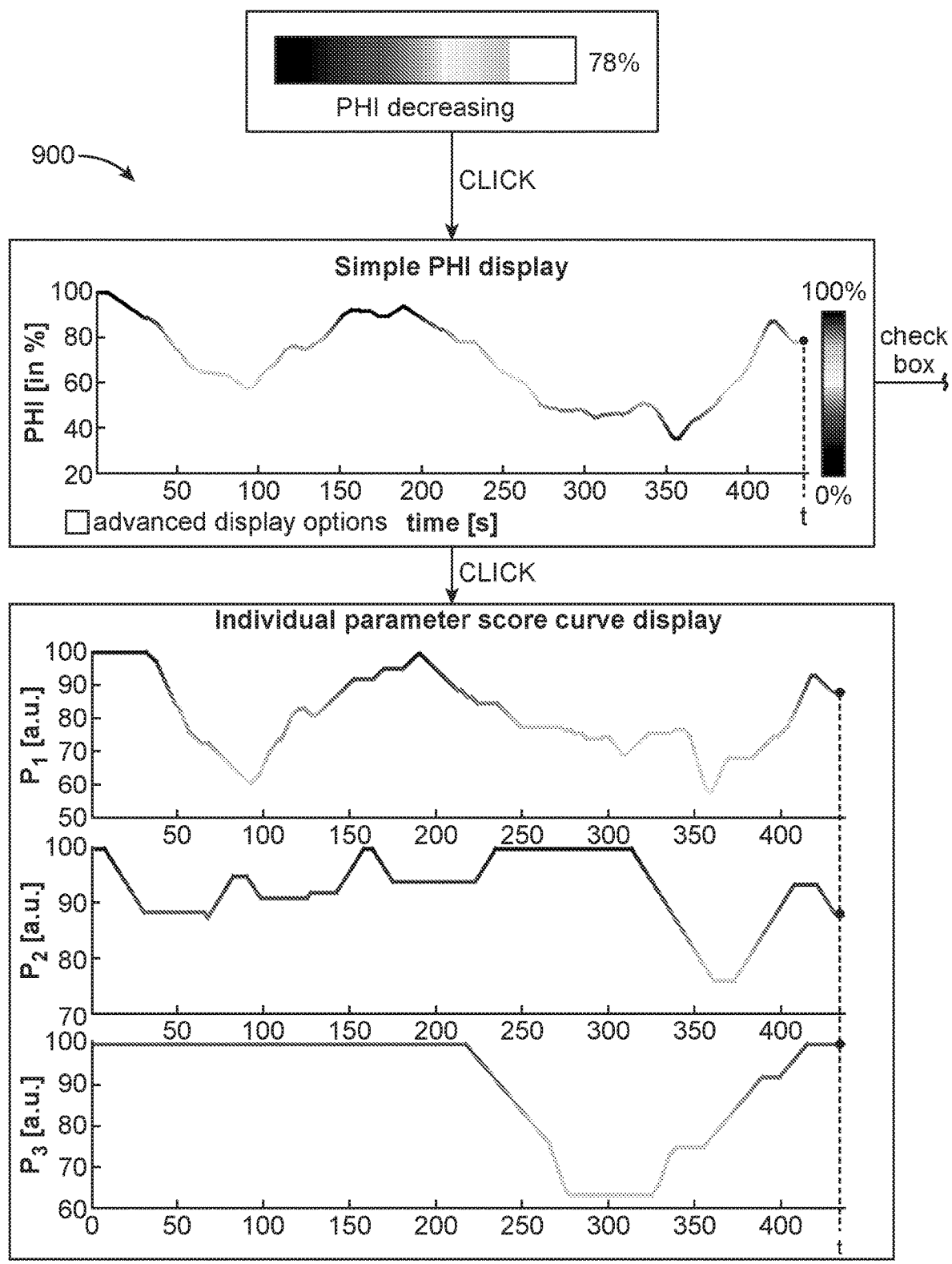
FIG. 9 is a graphical user interface view illustrating physiological parameter scores, patient health index values, and relative individual physiological parameter score contributions to the patient health index.
Figure 9:
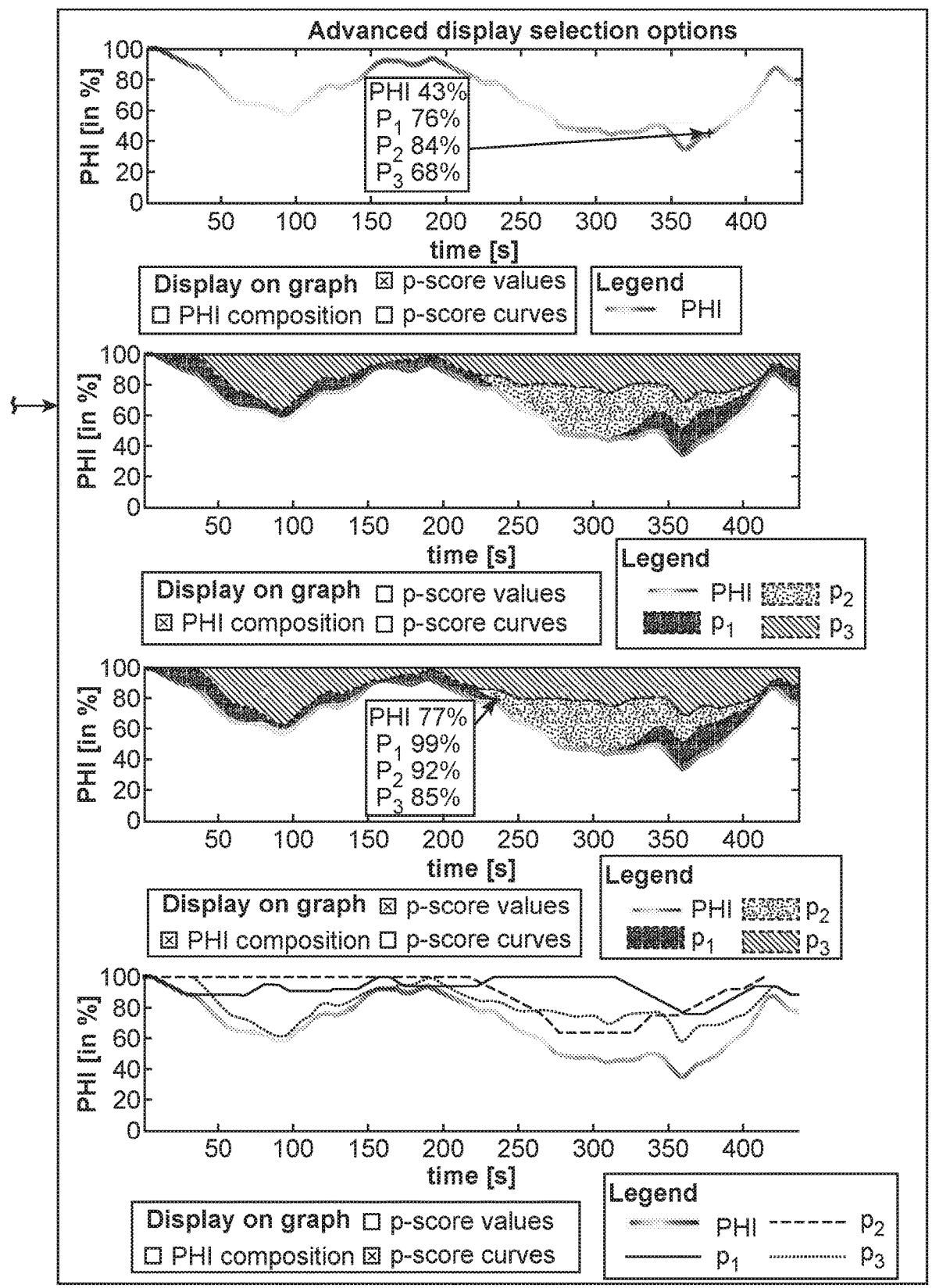

The graphical user interface displayed in the display 160 of the patient monitor, can render a three level visualization method as illustrated in diagram 900 of FIG. 9. At the highest level, the overall patient score can be given as a percentage number next to a coded bar (e.g., color coded bar, etc.) and an estimation of the current health development trend (decreasing/stable/increasing). Clicking on a graphical user interface corresponding to the bar can open a multi-parameter score (i.e. PHI) view over time that can be zoomed in and out (this view replaces the bar). Clicking on a graphical user interface element in the graphical user interface corresponding to the graph can further open individual parameter scores that result in the overall PHI so that the individual contributions can be assessed (this view replaces the overall PHI view). Clicking on a graphical user interface element corresponding to this view can bring back the initial bar.

The PHI visualization (middle level) can be further extended, for example, through, for example, check box graphical user interface element selection. This advanced display mode can allow for selection of different curves and values to be displayed within the same graph in the graphical user interface. Selection options can include, for example, displaying the PHI and all physiological parameter scores in the same graph or displaying the physiological parameter score values at a given time point. The time point can be selected by sliding the mouse (or finger for a touch screen, etc.) to the respective position of the PHI curve. The score values for the selected time point can be displayed in the graphical user interface in a box that automatically adapts its position so that it ideally does not cover the PHI curve. The values in the box can be instantaneously updated to the new mouse/finger position, i.e. they change with every small movement. Another option can be to display the relative physiological parameter contribution to the PHI. This arrangement is an intuitive way of conveying to the user the influence of each individual parameter on the current PHI (without overlaying all parameter curves in one graph, which might easily become confusing).

Figure 10:
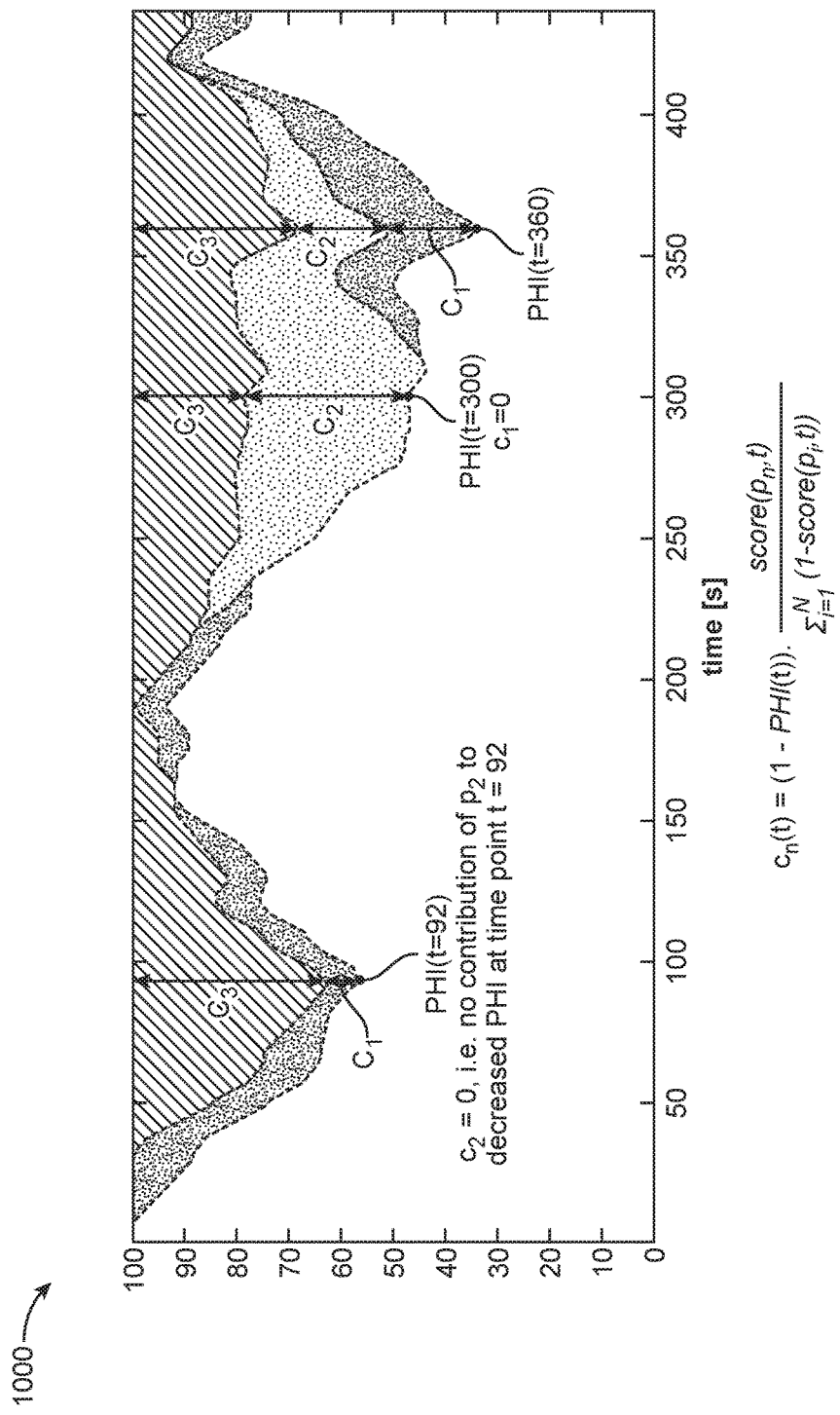
FIG. 10 is a diagram illustrating the calculation of relative individual parameter contributions to a patient health index for display on a graphical user interface.

The computation of the relative contributions is further elucidated in diagram 1000 of FIG. 10. For each parameter $p_n$ at time point t, its relative contribution $c_n(t)$ can be derived by scaling the amount of deviation of the PHI from 100% by the individual parameter score divided by the sum of all N individual score deviations from 100%. In other words, the value of $c_n(t)$, i.e. the thickness of the respective layer in the graph, can represent the relative influence that parameter n has had in the production of the PHI at the respective time point. For example, the PHI decrease at t=92 is only due to $p_1$ and $p_3$, since $p_2$ is perfect (100%). The parameter being mainly responsible for the PHI at this time point is $p_3$ as can be seen from the comparatively large $c_3$ value and small $c_1$ value.

While the above is described in reference to a patient monitor 130 which can, for example, be positioned next to the bedside of the patient 110, it will be appreciated that the PHI can be implemented by remote computing systems provided that the data streams from the physiological sensors 120 are made available (directly or over a computing network). Further, the algorithms provided herein can be used for retrospective analysis of the patient. For example, regions of low overall PHI directly point towards interesting periods for further investigation, without having to look at each individual alarm recorded. The physiological data can, in some cases, be automatically annotated for subsequent review because low patient health indices indicate clinically relevant events.

Figure 11:
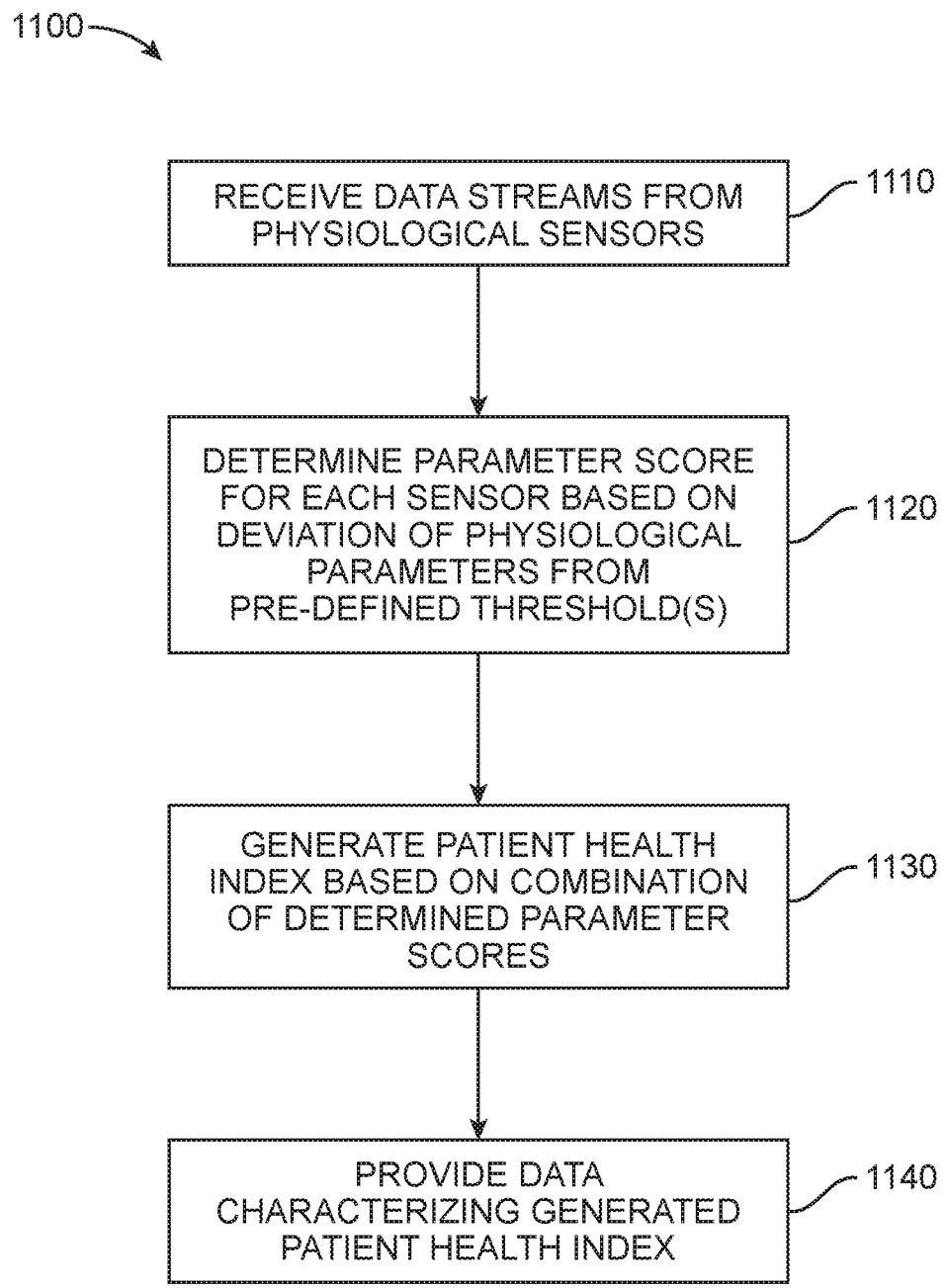
FIG. 11 is a process flow diagram illustrating computation and visualization of a patient health index.

FIG. 11 is a process flow diagram 1100 in which, at 1110, data streams are received from each of a plurality of sensors that include varying values generated by the sensor and which characterize an associated physiological parameter. A parameter score is then repeatedly determined, at 1120, for each physiological sensor that is based on whether the varying values for the associated physiological parameter deviate from at least one pre-defined threshold. A patient health index is repeatedly generated, at 1130, by combining each of the determined parameter scores to characterize an overall health of the patient. Data is then repeatedly provided, at 1140, that characterizes the patient health index score. Provided, in this regard, can include one or more of: displaying the data characterizing the patient health index score in an electronic display device, loading the data characterizing the patient health index score into the memory, storing the data characterizing the patient health index score in persistent memory, transmitting the data characterizing the patient health index score to a remote computing system, or generating an audio, vibrational and/or visual alert characterizing the patient health index score.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system can include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, can include machine instructions for a programmable processor, and/or can be implemented in a high-level procedural language, an object-oriented programming language, a functional programming language, a logical programming language, and/or in assembly/machine language. As used herein, the term "computer-readable medium" refers to any computer program product, apparatus and/or device, such as for example magnetic discs, optical disks, solid-state storage devices, memory, and Programmable Logic Devices (PLDs), used to provide machine instructions and/or data to a programmable data processor, including a machine-readable medium that receives machine instructions as a computer-readable signal. The term "computer-readable signal" refers to any signal used to provide machine instructions and/or data to a programmable data processor. The computer-readable medium can store such machine instructions non-transitorily, such as for example as would a non-transient solid-state memory or a magnetic hard drive or any equivalent storage medium. The computer-readable medium can alternatively or additionally store such machine instructions in a transient manner, such as for example as would a processor cache or other random access memory associated with one or more physical processor cores.

The computer components, software modules, functions, data stores and data structures described herein can be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality can be located on a single computer or distributed across multiple computers depending upon the situation at hand.

Figure 12:
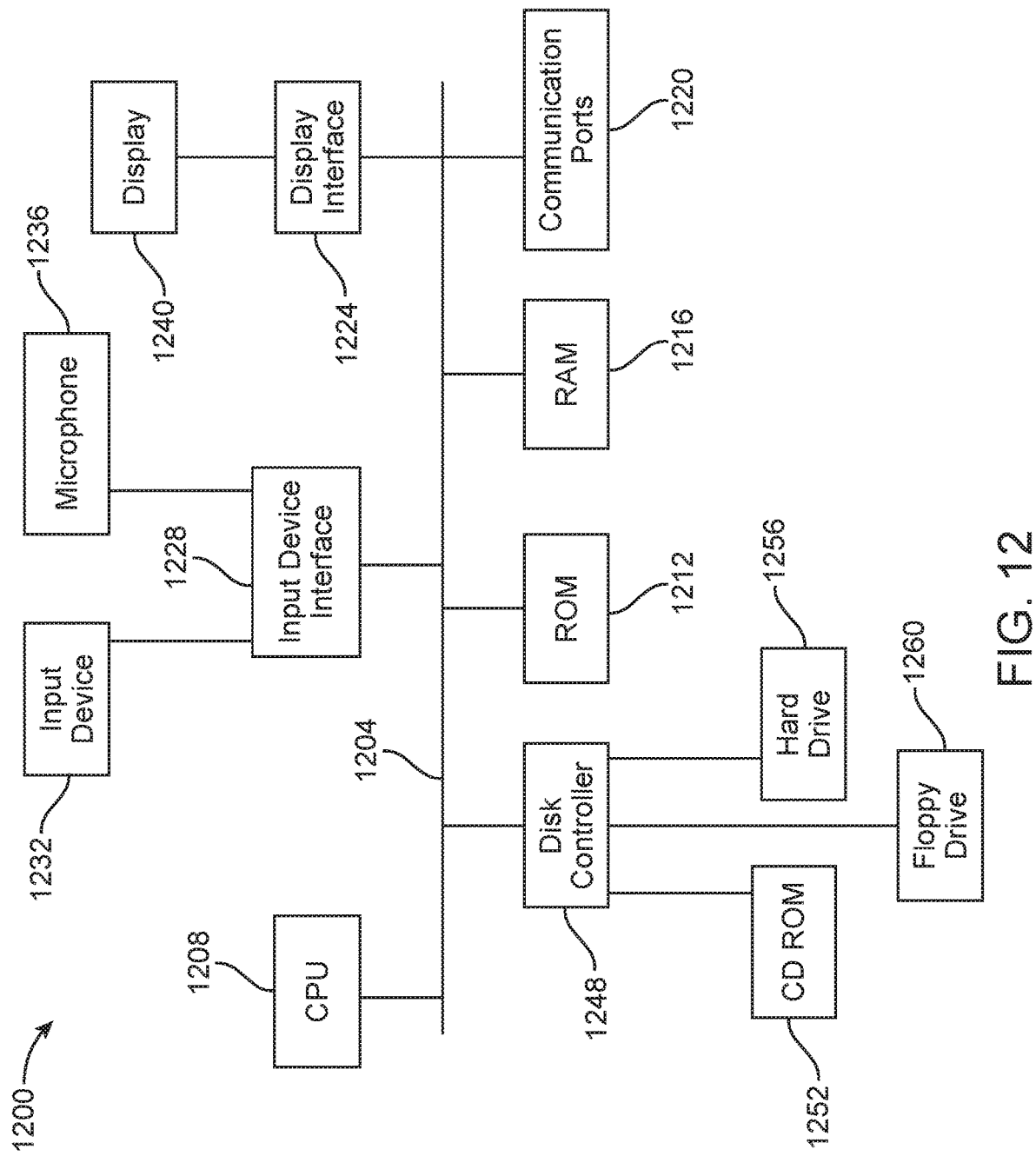
FIG. 12 is a diagram illustrating a computing device for implementing aspects of the current subject matter.

FIG. 12 is a diagram 1200 illustrating a sample computing device architecture for implementing various aspects described herein. A bus 1204 can serve as the information highway interconnecting the other illustrated components of the hardware. A processing system 1208 labeled CPU (central processing unit) (e.g., one or more computer processors/data processors at a given computer or at multiple computers), can perform calculations and logic operations required to execute a program. A non-transitory processor-readable storage medium, such as read only memory (ROM) 1212 and random access memory (RAM) 1216, can be in communication with the processing system 1208 and can include one or more programming instructions for the operations specified here. Optionally, program instructions can be stored on a non-transitory computer-readable storage medium such as a magnetic disk, optical disk, recordable memory device, flash memory, or other physical storage medium.

In one example, a disk controller 1248 can interface one or more optional disk drives to the system bus 1204. These disk drives can be external or internal floppy disk drives such as 1260, external or internal CD-ROM, CD-R, CD-RW or DVD, or solid state drives such as 1252, or external or internal hard drives 1256. As indicated previously, these various disk drives 1252, 1256, 1260 and disk controllers are optional devices. The system bus 1204 can also include at least one communication port 1220 to allow for communication with external devices (e.g., physiological sensors 120, etc.) either physically connected to the computing system or available externally through a wired or wireless network. In some cases, the communication port 1220 includes or otherwise comprises a network interface.

To provide for interaction with a user, the subject matter described herein can be implemented on a computing device having a display device 1240 (e.g., a CRT (cathode ray tube) or LCD (liquid crystal display) monitor) for displaying information obtained from the bus 1204 to the user and an input device 1232 such as keyboard and/or a pointing device (e.g., a mouse or a trackball) and/or a touchscreen by which the user can provide input to the computer. Other kinds of input devices 1232 can be used to provide for interaction with a user as well; for example, feedback provided to the user can be any form of sensory feedback (e.g., visual feedback, auditory feedback by way of a microphone 1236, or tactile feedback); and input from the user can be received in any form, including acoustic, speech, or tactile input. In the input device 1232 and the microphone 1236 can be coupled to and convey information via the bus 1204 by way of an input device interface 1228. Other computing devices, such as dedicated servers, can omit one or more of the display 1240 and display interface 1224, the input device 1232, the microphone 1236, and input device interface 1228.

In the descriptions above and in the claims, phrases such as "at least one of" or "one or more of" can occur followed by a conjunctive list of elements or features. The term "and/or" can also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system comprising:
   a communications interface configured to receive data streams from a plurality of physiological sensors, each of the plurality of sensors measuring a different physiological parameter of a patient;
   at least one programmable data processor; and
   memory storing instructions which, when executed by the at least one programmable data processor, result in operations comprising:
   receiving one or more data streams from each of the plurality of physiological sensors via the communications interface, the one or more data streams comprising varying values generated by the sensor and characterizing the associated physiological parameter;
   determining, at least once every five seconds, and for each of the plurality of physiological sensors, a parameter score;
   wherein determining the parameter score comprises, for each of the plurality of physiological sensors:
   calculating a magnitude of the varying values generated by the physiological sensor;
   determining which of three predetermined ranges the calculated magnitude falls into;
   allocating a first predetermined factor to the calculated magnitude when the calculated magnitude falls into a first of the three predetermined ranges, allocating a second predetermined factor to the calculated magnitude when the calculated magnitude falls into a second of the three predetermined ranges, and allocating a third predetermined factor to the calculated magnitude when the calculated magnitude falls into a third of the three predetermined ranges, the allocated factor being added to a time-average of allocated factors over a time window and used to generate the parameter score determined for the sensor, wherein the first, second, and third predetermined factors are the same for each of the plurality of physiological sensors;
   generating, at least once every five seconds, a patient health index by combining the parameter scores determined for each of the plurality of sensors to characterize an overall health of the patient; and
   providing, at least once every five seconds, data characterizing the patient health index.

2. The system of claim 1, wherein the providing the data comprises at least one of: displaying the data characterizing the patient health index in an electronic display device; loading the data characterizing the patient health index into the memory; storing the data characterizing the patient health index in persistent memory; transmitting the data characterizing the patient health index to a remote computing system; and generating an audio, vibrational and/or visual alert characterizing the patient health index.

3. The system of claim 1, wherein the operations further comprise:
   time-averaging the allocated factors over a pre-defined time window, the time-averaged allocated factors being used to generate the parameter score determined for each of the plurality of physiological sensors.

4. The system of claim 1, wherein the generating the patient health index comprises assigning a weight to the parameter score determined for each of the plurality of physiological sensors when combining the parameter score determined for each of the plurality of physiological sensors.

5. The system of claim 4, wherein the weight varies depending on an amount of time and/or a severity of the calculated deviation from the at least one pre-defined threshold.

6. The system of claim 1, wherein the operations further comprise:
   identifying segments of time during which the values in the data streams are unreliable; and
   adjusting the parameter score determined for each of the plurality of physiological sensors to exclude the identified segments of time during which the values in the data stream are unreliable.

7. The system of claim 6, wherein the adjusting comprises:
using values from preceding or successive segments of time relative to the identified segments of time for the identified segment of time when determining the parameter score for each of the plurality of physiological sensors.

8. The system of claim 6, wherein the adjusting comprises:
using factors from preceding or successive segments of time relative to the identified segments of time for the identified segment of time when determining the parameter score for each of the plurality of physiological sensors.

9. The system of claim 1, wherein the providing the data comprises:
displaying, in a graphical user interface, a visualization displaying the repeatedly generated patient health index over time in relation to the parameter score repeatedly determined for each of the physiological sensors.

10. The system of claim 9, wherein the visualization further displays parameter scores used to generate the repeatedly determined patient health index.

11. The system of claim 10, wherein a color of at least a portion of the visualization varies depending on the allocated factors.

12. The system of claim 9, wherein the visualization further displays at least one of the pre-defined thresholds.

13. The system of claim 12, wherein a color of at least a portion of the visualization varies depending on deviations from the pre-defined thresholds.

14. A method for a system including a communications interface configured to receive data streams from a plurality of physiological sensors, each of the plurality of physiological sensors measuring a different physiological parameter of a patient, the method comprising:
receiving, from each of the plurality of physiological sensors, data streams comprising varying values generated by the sensor and characterizing an associated physiological parameter;
determining, at least once every five seconds, and for each of the plurality of physiological sensors, a parameter score wherein determining the parameter score comprises, for each of the plurality of physiological sensors;
calculating a magnitude of the varying values generated by the physiological sensor;
determining which of three predetermined ranges the calculated magnitude falls into;
allocating a first predetermined factor to the calculated magnitude when the calculated magnitude falls into a first of the three predetermined ranges, allocating a second predetermined factor to the calculated magnitude when the calculated magnitude falls into a second of the three predetermined ranges, and allocating a third predetermined factor to the calculated magnitude when the calculated magnitude falls into a third of the three predetermined ranges allocated factor being added to a time-average of allocated factors over a time window and used to generate the parameter score determined for the sensor, wherein the first, second, and third predetermined factors are the same for each of the plurality of physiological sensors;
generating, at least once every five seconds, a patient health index by combining the parameter scores determined for each of the plurality of sensors to characterize an overall health of the patient; and
providing data characterizing the patient health index at least once every five seconds.

15. A non-transitory computer readable medium storing instructions, which when executed, cause a system to execute a method, the system including a communications interface configured to receive data streams from a plurality of physiological sensors, each of the plurality of sensor measuring a different physiological parameter of a patient, the method comprising:
receiving, from each of the plurality of physiological sensors, data streams comprising varying values generated by the sensor and characterizing an associated physiological parameter;
determining, at least once every five seconds, and for each of the plurality of physiological sensors, a parameter score wherein determining the parameter score comprises, for each of the plurality of physiological sensors;
calculating a magnitude of the varying values generated by the physiological sensor;
determining which of three predetermined ranges the calculated magnitude falls into;
allocating a first predetermined factor to the calculated magnitude when the calculated magnitude falls into a first of the three predetermined ranges, allocating a second predetermined factor to the calculated magnitude when the calculated magnitude falls into a second of the three predetermined ranges, and allocating a third predetermined factor to the calculated magnitude when the calculated magnitude falls into a third of the three predetermined ranges, the allocated factor being added to a time-average of allocated factors over a time window and used to generate the parameter score determined for the sensor, wherein the first, second, and third predetermined factors are the same for each of the plurality of physiological sensors;
generating, at least once every five seconds, a patient health index by combining the parameter scores determined for each of the plurality of sensors to characterize an overall health of the patient; and
providing data characterizing the patient health index at least once every five seconds.

* * * * *